(12) United States Patent
Maldonado et al.

(10) Patent No.: US 7,015,156 B2
(45) Date of Patent: Mar. 21, 2006

(54) PERFUMED ABRASIVE PAD AND MANUFACTURING PROCEDURE

(75) Inventors: Raul Maldonado, San Luis Potosi (MX); Efren Perez, Mexico City (MX)

(73) Assignee: 3M Innovative Properties Company, St. Paul, MN (US)

( * ) Notice: Subject to any disclaimer, the term of this patent is extended or adjusted under 35 U.S.C. 154(b) by 23 days.

(21) Appl. No.: 10/483,880

(22) PCT Filed: Jul. 13, 2001

(86) PCT No.: PCT/MX01/00048

§ 371 (c)(1),
(2), (4) Date: Jul. 12, 2004

(87) PCT Pub. No.: WO03/005876

PCT Pub. Date: Jan. 23, 2003

(65) Prior Publication Data

US 2004/0242133 A1 Dec. 2, 2004

(51) Int. Cl.
*B32B 5/18* (2006.01)
(52) U.S. Cl. ............ 442/375; 442/327; 442/374; 15/208; 424/401; 428/402.2; 428/402.21; 428/403
(58) Field of Classification Search .......... 15/208, 15/209.1; 424/401, 402, 408, 417; 428/402.2, 428/402.21, 403; 442/327, 374, 375
See application file for complete search history.

(56) References Cited

U.S. PATENT DOCUMENTS

| | | | |
|---|---|---|---|
| 2,958,593 A | 1/1960 | Hoover et al. | |
| 3,516,941 A | 6/1970 | Matson | |
| 4,514,461 A | 4/1985 | Woo | |
| 4,882,220 A | 11/1989 | Ono et al. | |
| 4,917,920 A | 4/1990 | Ono et al. | |
| 5,547,479 A | 8/1996 | Conwell et al. | |
| 5,876,266 A | 3/1999 | Miller et al. | |
| 6,017,351 A | 1/2000 | Street | |
| 6,094,766 A | 8/2000 | Nash et al. | |

FOREIGN PATENT DOCUMENTS

| | | |
|---|---|---|
| GB | 1374272 | 11/1974 |
| GB | 1401143 | 7/1975 |
| JP | 52-31200 | 3/1977 |
| JP | 53-49200 | 5/1978 |
| JP | 53-106885 | 9/1978 |
| JP | 53-47440 | 12/1978 |
| JP | 54-4886 | 1/1983 |
| MX | PA/A/2000/010268 | 5/2002 |
| WO | WO 99/51401 | 10/1999 |

OTHER PUBLICATIONS

Advantage Maintenance Products Ltd; [Currently p. 19, updated on the internet 2004]; [Retrieved from the internet on Apr. 9, 2004]; http://www.whitemop.com/catalog/24.html.

*Primary Examiner*—Arti R. Singh
(74) *Attorney, Agent, or Firm*—Trisha D. Adamson; David B. Patchett

(57) ABSTRACT

The a present invention is related to an abrasive cleaning article, made of spread abrasive particles and microencapsulated particles of an aromatizing substance contained in urea-formaldehyde walls, through a three-dimensional non-woven web of fiber that are bonded to the web by a resin adhesive. The item, of any geometric shape, offers the user a sensation of cleanliness due to the constant presence of a "fresh" scent associated to the fiber; the scent remains during the whole life of the abrasive item since the microcapsules break partially during the normal use of the item. The invention also refers to the production process of such abrasive item.

12 Claims, No Drawings

PERFUMED ABRASIVE PAD AND MANUFACTURING PROCEDURE

TECHNICAL FIELD

The present invention is related to an abrasive article for cleaning and scouring, and any other similar home and industrial applications, and in a more specific manner, an abrasive product made of a three-dimensional non woven fabric that has an aromatic substance incorporated in microcapsules that are broken through the mechanical effect of the regular use of the abrasive article, during the whole life of the article.

BACKGROUND

The abrasive products with a non-woven base are totally known. Many of the commercially available products are made of a web of non-woven synthetic fibers to which hard abrasives finely divided such as silica carbide, alumina and silica, are added. Other soft abrasives include calcium carbonate, talc, and synthetic polymer resins. In repeated occasions, as an example of such fibers the previous art mentions, the one commercialized under the "Scotchbrite" and "Buf Puf" brand from Minnesota Mining and Manufacturing Co, which contains aluminum-oxide particles in a way that abrasive power is reinforced.

It has been widely recognized that in many cleaning applications, specially in home applications, housewives or users of the said abrasive item, discard it when the bad odor is evident and constant, even when the item maintains its abrasive properties. As a consequence, there is an excessive expenditure when replacing abrasive items, as well as a waste of useful material.

An alternative to avoid such situation is to incorporate perfume or fragrance to the cleaning items, for example, to those designed for toilets and kitchens in order to provide a fresh aroma or scent to the treated surfaces and to the surrounding environment, but problems have been found to achieve this.

The previous art describes some intents for aromatizing cleaning articles, such as the described in the British Patent GB 1,374,272 (Bayliff A., Geoffrey, 1974) regarding the impregnation of cleaning pads, stating that the fabric is saturated with perfume, with the inherent problems of personnel discomfort or contamination of other products manufactured in the same facilities, or, the fact that a perfume appropriate for a toilet might not be acceptable for other products. Another problem is the storage of the aromatized product along with other products, and that the package is not hermetic. Another problem is the waste of perfume due to evaporation when the product is manufactured and stored.

Therefore, an important feature of such products is their ability to extend their performance for a long period of time while retaining certain amounts of the functional ingredients (perfumes) while only a portion of such ingredients is exposed to the surrounding environment. The control of the release ratio can be achieved in a variety of manners, including diffusion by means of the voids in the web, forcing the ingredient to the surface by compressing the voids and breaking the spheres or internal cells of the matrix of the support material. A solution described in this patent is to include fragile capsules, of a very small size and filled with perfume, that can be incorporated to the filler of a cleaning pad; an alternative mode is to use capsules with water soluble walls, which dissolve precisely when pad gets wet for its use. It is suggested that the perfume is oily or oil-based. The pad fabric can be pulp, crepe fabric or non woven waste material; the capsules can be spread in the filler material by means of an adhesive or by means of printing, as a viscous mixture or in an appropriate diluter or even as an effervescent tablet.

U.S. Pat. No. 4,514,461 (Yen-Kong Woo, 1985) describes a cloth saturated with microscopic spheres in the form of fragile capsules, inside the voids of the internal fibers of the cloth fabric, that can be woven or non woven, in such a manner that the spheres remain in the cloth and can be invisible in its surface so the appearance is not altered. The cloths described in the latter patent include, cotton, wool, silk and other synthetic cloths.

The process used to emboss the microparticles in the cloth is made of three stages: a) spraying or saturating the cloth with the capsule solution into an adhesive such as acrylic latex; b) rolling between two hot rollers with the same pressure and temperature to ensure a deep and consistent penetration and to remove the particles in the surface and c) adhesive curing.

U.S. Pat. No. 4,882,220 y U.S. Pat. No. 4,917,920 (Ono, Akira et al, 1989, 1990) describe an aromatic fibrous structure, made of cloth or a similar material, with microcapsules containing perfume; the microcapsules are made of an external wall with a formaldehyde based resin from the urea-formaldehyde resin and melamine-formaldehyde type. The microcapsules are bonded to a fibrous base of 0.7 denier or less which hold the microcapsules in the voids of the fibrous structure.

The manufacturing process of the fabric is described in patent '920, and includes the application of a liquid containing microcapsules made of a formaldehyde-based resin wall, an aromatic substance and a prepolymer substance of thermally reactive organopolysyloxane, and a drying process for the fibrous structure with a temperature below 150° C., to bond the microcapsules.

The description of the previous art of the said patents makes a very thorough review of the intents for applying an aromatic substance to what they call a "closed system" (encapsulating in microcapsules) to a fibrous structure, and then converting the closed system into an "open system" by breaking the microcapsules by means of efforts applied to the microcapsules in order to release the fragrance during the fibrous structure use. The following is mentioned as previous art: an application method for a mixture of microcapsules containing a liquid for toilets with a coating of adhesive containing a melamine resin, a cloth (British patent 1,401,143); an adhesion method for the microcapsules containing perfume, with the aid of a capsule remover mainly containing a cationic organic substance such as ammonia quaternaries or similar substances and a non-ionic organic substance such as esters or sorbitan or similar substances (Japanese application 52-31,200); a method to prepare aromatic towels by applying a liquid mixture of microcapsules containing perfume with an acrylic resin, cloth for towels (Japanese patent application 58-4,886); a method to prepare fragrance releasing printed cloth by printing a paste made of thermoplastic material, a thickening agent and microcapsules containing perfume (Japanese patent application 53-47,440 y 53-49,200); a method to prepare printed cloth that release a fragrance by thermal transference of an adhesive layer made by a pigment, a high molecular weight resin, perfume microcapsules, etc. to a cloth (Japanese application 53-106, 885).

All of these methods offer a poor bond that results in a low washing resistance. The use of high temperatures, even when bonding is improved, results in problems such as denaturalization of the perfume, or microcapsule collapsing due to perfume vaporization occurring due to high temperature.

There is an emphasis on the fact that nylon fibers, due to their smoothness, make appropriate bonding difficult.

The active ingredient release from the microcapsules, can be achieved by diffusion, volatilization, pressure or stirring. The release can be gradual when simple diffusion or volatilization are involved, or, on demand, when pressure, stirring or a combination of techniques are involved. The particles themselves can be rigid or compressible. The encapsulated substance tends to be fluid, including volatile and non-volatile liquids or solutions, a soluble solvent or a solid with a low fusion point or a semi-solid. The release on demand can be achieved, depending on the product features by:
a) An external mechanical effort, pressure or rubbing of the article on a surface for which the active substance intended,
b) Wall fusion, by heat application, for example, on such articles intended to be used near the human body,
c) Dissolution in the media in which they are added, due to the contact with a solvent, body parts or other liquids.

The use of particles (spheres or microcapsules) as a mechanism to retain the active substances, provides a better control on their release than the systems where the fiber matrix is directly impregnated with the substances, as described above in the reference to patent GB 1,374,272.

When the release is controlled, it occurs in a more sustained manner giving a continuous and fresh supply to the fiber matrix and to the environment in which the matrix is placed or to the surface with which it has contact.

Finally, it is important to say that the documents mentioned up to this point and that are regarded as previous art, the incorporation of microcapsules with active ingredients such as perfume and fiber matrix support, are limited to woven and non-woven cloth, intended to manufacture clothing or similar products, but there are no references of fiber matrixes of a higher thickness, intended for abrasion, scouring and cleaning, which is the objective of the present invention.

There are, however, some references that indicate the obvious interest of incorporating a series of improvements to the cleaning and abrasive item properties to use microcapsules of active ingredients other than perfume, or, the use of fragrances as a value added to the primary function of the articles:
U.S. Pat. No. 5,876,266 (Miller et al, 1999) describes a polishing pad made of semiconductor waffles, where the pad has microcapsules with a polishing agent; the release is controlled by a polishing parameter.
Patent application WO 99/51401 (Cheyne, Robert, 1999) describes an abrasive pad for domestic use, specially for kitchen and baths, with a non-woven matrix in which an antimicrobial compound is spread.
The other reference, from the site http://www.whitemop.com/catalog/24.html, shows a pad for polishing floors manufactured with natural coconut fiber, that releases a "fresh coconut" fragrance when the pad is moistened with coconut oil. The odor release occurs when the polisher is on with the pad moistened with coconut oil, which is added in a liquid form.

The information herein is deemed as representative of the state of the current techniques, and has been mentioned so a person with knowledge on the subject can establish that it does not interfere with the matter of the present invention described below.

OBJECTIVES OF THE INVENTION

Due to the problems of the different types of cleaning fibers in the previous art that have not being solved, the invention described herein has the following objectives:

The main objective of the present invention is to provide an improved cleaning product, which generates a nice aroma during its use. This product consists of a simple non woven matrix that is the same as its extension, made of a three-dimensional non woven structure made of a non woven material besides to a second extension of this type of structure that consists of a three-dimensional non woven structure made of laminated non woven material and adhered on a natural or synthetic foam, that can be for example of polyurethane or cellulose.

The other objective of the invention, is that the cleaning item leaves the user with a sense of cleanliness due to the odor that is associated with the removal of dirt or filth of the surfaces that are washed, for example, kitchen utensils, stoves, sinks, etc.

Another objective of the present invention is that the added aroma remains during the whole life of the product.

Another objective of the present invention is to allow for the optimum use of the life of the cleaning article, preventing its early discard due to bad odor release, when the article still keeps its abrasive properties, decreasing unnecessary expenses.

Another objective of the present invention, is to describe the microcapsule incorporation process over the three-dimensional non woven structure made of a non woven material, where the microcapsules may contain, as an extension application of this type of structure, not just perfumes or fragrances as aromatic elements, but also antibacterial and fungicides as disinfectant elements, detergent, soaps, grease remover, tensoactives as a clean agents or exfoliant, astringent and vitamin as a facial cleansing compounds or general skin cleansing compounds.

BRIEF DESCRIPTION OF THE INVENTION

The present invention refers to a novel cleaning article, consisting of non-woven abrasive fiber, belonging to the type of fibers commonly known in the market, that have a web or matrix support made of nylon non-woven polymeric fibers with high tenacity, low tenacity or recycled, or polyester fiber coated with spread by means of a three-dimensional web of non-woven fibers, and bonded to it by means of a phenolic resin adhesive or latex; such cleaning item, for example, the abrasive fiber Scotch-Brite® or Buf Puf® from Minnesota Mining and Manufacturing Co, improved by the incorporation of microcapsules as described by Matson in patent U.S. Pat. No. 3,516,941 with an oil based perfume encapsulated that is released into the environment by breaking the spheres using the scouring mechanical action of the cleaning item on the surface to be treated.

The manufacturing process for the abrasive fiber is well known in the art and its main stages are:
a) Preparing the fibrous non-woven substrate starting from polymer fibers,
b) Applying a mud with the abrasive particles, pigment and additive in a suspension using the Roll Coat process, which is known in the art,
c) Applying a mud layer with similar features to the mud mentioned above, by spray coating one or both faces of the fiber substrate,
d) Curing the resins in an oven.

The microcapsule incorporation is made in the mud that is applied to the substrate during the roll-coat and spray-coat stages.

Microcapsules with urea structures are currently used in textile, medical and cosmetic applications. One of their main qualities is that by means of mechanical efforts the particles can be broken in order to release the oil-based fragrance in them. This feature is required in order to insure that the microcapsules withstand the process conditions and their permanence in the non-woven substrate for a period of time similar to the life of the abrasive item.

The microcapsules as the described in patent U.S. Pat. No. 3,516,941 by Matson, are an example of the microcapsules that can be used in cleansing pads of this invention.

DETAILED DESCRIPTION OF THE INVENTION

The web to be used in the present invention is, preferably an open non-woven web made of fibers that would preferably be joined one to the other in their mutual contact points by a prebonding cured resin. The appropriate non-woven web to be used in the item of the invention can be made from an air-supported construction, cloth, piquet, twisted, wet woven and fusion. A preferred mode of the invention is the non-woven web made of a non-woven, air-supported, three-dimensional, lifted, open substrate, such as the one described by the U.S. Pat. No. 2,958,593 Hoover et al.

The web is made of an appropriate synthetic fiber capable of standing the temperatures in which the resins and adhesives cure without deteriorating. The appropriate fibers for the use of the items in the invention include natural and synthetic fibers, and blends of both; the synthetic fibers preferably include those fibers made of polyester (for example, polyethylene-fteretalate), high or low resilience nylon (for example, hexamethylene-adipamide, polycaprolactame), polypropylene, acrylic (formed from acrylonitrile polymer), rayon, cellulose acetate, chloride copolymers of vinyl-acrylonitrile, and others. The appropriate natural fibers include those coming from cotton, wool, jute, and hemp.

The non-woven web is easily formed in a "Rando Weber Machine" (from Rando Machine Company, New York) or by means of other conventional methods.

The fiber of 6,10,13,17,70,110,120 and 200 denier that is used in the preferred mode of the invention, and that is a very convenient material for the non-woven synthetic fiber web, is Nylon staple 6.6 polyamide, with a circular cross section; such fiber forms the non-woven web; the output weights of the fiber at the end of the veil forming stage vary between 100–200 g/m$^2$.

The non-woven web is then submitted to a coating procedure in which the adhesive or coating primer is applied to the web, e.g., by a roll-coating.

On a later stage, the web is subject to a new coating by spraying or spray coating. The particle sprayer receives a mixture of air/abrasive particle coming form a fluid bed. The abrasive particles and microcapsules are fluidized in the bed by means of fluidizing air. The speed of the fluidizing air flow should be high enough so the fluidization can occur, and without being too high so "wormholes" are formed across the bed.

Such coatings are well known in the art and do not need further description in this document. Finally, the coated web goes through resin curing before it is rolled and/or cut for its distribution and use.

The appropriate particles to be included in the abrasive items of the present invention include all the known fine abrasive particles like aluminum oxide, silicon carbide, silicates, talks, carbonates, including polymeric particles such as PVC, melamine or Ultra high Molecular Weight Polyethylene UHMWPE. Preferably, such fine abrasive particles have a size distribution of an average diameter of 10–250 microns or less.

Among the various types of abrasive minerals that are useful for the present invention are aluminum oxide particles, including ceramic aluminum oxide, heat treated aluminum oxide and melted which aluminum.

The formulations to be used in the preferred mode of this invention are as follows:

TABLE 1

Preferred composition of the abrasive coating.

| COMPONENT | PERCENTAGE |
|---|---|
| Phenolic Resin | 20–65 |
| Pigment | 0.5–1.0 |
| Water | 12–30 |
| Abrasive element such as the described in the text | 15–65 |
| Surfactant | 0.5–1.5 |
| Microcapsule with perfume | 0.001–15 |

Where all the stated amounts are expressed as weight percent and where:

The phenolic resin is used as a pre-bonding resin to join fibers to each other in their contact points, this resin is water-based an d phenolic, obtaining an added dry weight between 150–300 g/m$^2$. The mineral particles and the perfume microcapsules are randomly distributed in the fiber fabric, anchoring to it by means of the phenolic resin and extending across the web to the inside and to the outside. The duration of the final product is ensured by the strength provided by the phenolic resin.

The pigment is a water base colorant dispersion which provides the required color to the material. Adding the pigment is a response to the need to offer the user an easy way to identify the abrasive level o the available item, and different colors could be used for the different abrasive levels of the final product.

The mineral aluminum oxide is made of mixtures of the following compounds:

TABLE 2

Preferred composition of the abrasive mineral.

| COMPONENT | PERCENTAGE |
|---|---|
| Aluminum oxide | 94.5% +/− 1.5% |
| Titanium oxide | 3.0% +/− 0.4% |
| Silica | 1.4% +/− 0.8% |
| Ferric oxide | 0.5% +/− 0.1% |

The surfactant has the function of homogenizing the mixture so it can be applied to the fiber substrate; an example of the surfactant to be used is the commercially available Surfynol DPM104 or CT171, as it is described in the Mexican patent application number PA/a/2000/010268 (Maldonado, 2000).

The microcapsules with perfume are produced from a mixture of ingredients consisting of:

TABLE 3

Preferred composition to form perfume microcapsules.

| COMPONENT | PERCENTAGE |
| --- | --- |
| Decamethylcyclopentasiloxane | 35–40 |
| Oil base fragrance | 25–30 |
| Urea | 15–25 |
| Water | <2 |
| Octamethylcyclotetrasiloxane | <2 |
| Formaldehyde | <0.04 |

The rest of the ingredients of the microcapsules are the related to the composition of the ingredients contained inside. Matson, in U.S. Pat. No. 519,641 shows the mechanism for creating a with the formulation shown in Table 3. Both the slurry and the pale yellow powder contain an oil base fragrance in the structure of polyoxymethyleneurea, which allows for its further incorporation to the phenolic resin as stated in table 1.

The microcapsules with the oil base fragrance inside, both in their liquid form (slurry) as well as dehydrated are appropriate additions to the abrasive formulations so an aroma can be developed in the washing solution and in the fiber itself, due to the fact that the urea structure that surrounds the microcapsules can be broken when a physical effort of the magnitude of the effort applied to the fiber when it is used to treat surfaces such as ceramic, steel, aluminum, glass, melamine, PVC, anti-adherent materials, iron and others present in common domestic and industrial applications, is exerted.

Some of the problems found when trying to incorporate the microcapsules with a fragrance to the abrasive fibers are the following:

(1) The materials to be used should not affect the phenolic resin based adhesives used in fiber manufacturing, so the regular performance of the finished product is what the user knows.

(2) The microcapsules should stand the pressure and temperature of the fiber manufacturing process. Otherwise, the microcapsules would be absent from the finished product and the perfume would volatilize into the factory environment.

(3) The microcapsules should be subject to be broken under the normal use conditions of the fiber, so the effective release of the contained fragrance is ensured.

(4) The microcapsules should not have porous walls that enable the diffusion, of their content to the outside, which would result in losing the perfume to the environment.

(5) The microcapsule walls should not be highly water soluble or highly soluble in aqueous media such as the expected conditions in the product regular operations, so the depletion of the perfume in an early stage of the life of the product is avoided.

The selection of urea-formaldehyde walls for the microcapsules is based on some of the properties set forth regarding other varieties of microcapsules, including:

(1) They have a chemical composition that make them compatible with phenolic resin, the main component of the abrasive fibers.

(2) The chemical structure is also appropriate to be suspended in the phenolic resins (Neste-Dynea Co.), acrylic resins, latex (Rohm & Hass Co.), estirene-butadiene resins (allard Creek Co. LTD.), vinylethylene acetate emulsions (Air Products Co.), EVA molecule resins and other resins commonly used in non-woven substrate applications.

(3) The microcapsule structure of polyoximethyleneurea is strong enough and stable enough to stand three critical phases of the fiber manufacturing process: Roll coat, Spray coat curing.

(4) The same structure allows also for the microcapsules to be broken by the mechanical effort of the regular abrasive fiber use, so there are no additional operations or efforts required for the aroma to be released from the finished product.

(5) A variant of the same objective of the present invention is the fact that the same microcapsule structure but with different hardness levels, permits the release of efforts the different contained elements within microcapsules by different mechanical with varying degrees of rupture of the microcapsule.

To determine the operation conditions in the critical stages of the process, test batteries for fragrant fibers manufacturing have been conducted, with the following results:

TABLE 4

Relationship between the amount of microcapsules and the fragrance.

| Microcapsule Concentration Roll Coat (%) | Microcapsule Concentration Spray Coat (%) | Grade (identification level of the users) |
| --- | --- | --- |
| 4.0 | 4.0 | 7.0 |
| 2.0 | 2.0 | 5.2 |
| 0.0 | 0.0 | 0.5 |
| 0.0 | 4.0 | 2.0 |
| 4.0 | 0.0 | 4.6 |

All expressed in weight percent.

Where the grade 0 corresponds to the minimum identification level, while the 7 corresponds to the maximum level of identification of the fragrance by smelling, by a panel of abrasive fiber users. These results were used to create a model that describes the relationship between microcapsule concentration and roll coat or spray coat, with the identification level by smell of the users.

Table 4 establishes the relationship found in the present invention, between the microcapsule concentration and the fragrance identification level by the users. The developed model for the invention to manufacture perfumed abrasive fibers explains that the recommended amount is for microcapsules in the adhesive agent or bond that provides the best results for the users under normal conditions of home or commercial use. The performance noticed on table 4 is applicable to the material combinations described by the previous art.

The relationship between the formulation components show the importance found in a higher concentration of microcapsules in the roll coated adhesive, compared to the spray coat stage, so the best identification level of the fragrance is achieved by the users (example: 4:1, 3:2).

The manufacturing process with the recommended amounts in this description, establishes the amount of microcapsules in the adhesives in the Roll Coat and Spray Coat stages that provide the best results for the fragrance identification level by the users.

The three-dimensional non woven production containing the non woven abrasive element in which the microencapsulated fragrance or perfume are contained can be obtained with the preferred operation conditions shown in the following table:

TABLE 5

Operation Condition Ranges.

| Condition - Stage | Range |
| --- | --- |
| Roll Pressure - Fiber substrate moistening by roll coating | 30–90 kg/cm$^2$ |
| Nozzle Pressure - mineral spraying on the semi-finished fiber | 3–5 kg/cm$^2$ |
| Oven Temperature - Phenolic resin cure. | 120–150° C. |

These conditions allow for microcapsules, both mixed and dehydrated, to be uniformly deposited through all the fiber substrate thickness without having a loss or microsphere degradation.

To estimate the permanence of the perfume microcapsules during the life of the product, test were conducted, testing a series of sample fibers under conditions similar to normal use, using washing machines with a circular agitator with a range of 1230 to 1250 rpm, with a space of 0.04277 m$^3$, obtaining:

TABLE 6

Use Simulation Results.

| Simulation Time (minutes) | % of users that identified the fragrance when gel detergent is not included | % of users that identified the fragrance when gel detergent is included |
| --- | --- | --- |
| 10 | 100 | 95 |
| 20 | 90 | 80 |
| 30 | 75 | 65 |
| 40 | 60 | 45 |
| 50 | 45 | 25 |
| 60 | 20 | 12 |

Where the simulation time is equivalent to an estimated scale, to the use that the item would have using it during 30 minutes, 15 days after the application, and during 60 minutes, 30 days after the application. It is observed that the fragrance produced by the present microcapsules can be identified 30 days after the application, which is the life of the design for a three-dimensional non woven structure made by a non woven material of the "Scotch-Brite" fibers by Minnesota Mining and Manufacturing co. A similar study applies to facial products of the type of Buf Puf® from the same company.

What is claimed is:

1. An abrasive cleaning article that generates an aroma during use, said article comprising:
   (a) a three-dimensional non-woven web of fibers;
   (b) abrasive particles adhesively bonded to the fibers; and
   (c) microcapsules including an aromatic substance adhesively bonded to the fibers, wherein the aromatic substance is released from the microcapsules during the normal use of the article to produce an aroma.

2. The abrasive article according to claim 1, wherein said aromatic substance is encapsulated in said microcapsules and said microcapsules release their content when they are broken due to the normal use of the article.

3. The abrasive article according to claim 2, wherein the microcapsules are made with polymer walls of the urea-polyoximethylen type.

4. The abrasive article according to claim 3, wherein the microcapsules have different sizes and different wall resistant whereby the aromatic substance can be released with the different mechanical efforts exerted by its use.

5. The abrasive article according to claim 1, wherein the microcapsules are bonded to a natural or synthetic foam such as polyurethane or cellulose.

6. The abrasive article according to claim 1, wherein said microcapsules further include an ingredient directed to skin care.

7. The abrasive article according to claim 1, wherein the aromatic substance is oil-based and selected from the different natural and synthetic perfumes or fragrances with functional groups and essential extracts, slurries or oils.

8. The abrasive article according to claim 1, wherein the abrasive particles are dispersed through the web and bonded to the fibers, and further wherein said particles are fine abrasive material particles selected from the group consisting of aluminum oxide, silicon carbide, silicates, talcs, carbonates, or polymeric particles such as PVC, melamine or Ultra High Molecular Weight Polyethylene (UHMWPE).

9. The abrasive article according to claim 1, wherein the microcapsules contain antibacterial and fungicides as disinfectant elements, detergent, soaps, grease remover, tensoactives as a cleansing agents or exfoliating agents, astringent and vitamin as a facial cleansing compounds or general cleansing.

10. The process to manufacture an abrasive fiber with encapsulated perfume, comprising the steps of:
   a) preparing a non-woven web of polymeric fibers;
   b) applying slurry at least to a face of the non-woven web by means of roll coating with rollers covered with the slurry;
   c) spray coating the slurry at least on a face of the non-woven web;
   d) curing the polymers contained in the slurry in an oven;
   wherein the slurry in stages (b) and (c) comprises:

| | |
| --- | --- |
| 20–65% | Phenolic Resin |
| 0.5–1.0% | Pigment |
| 12–30% | Water |
| 15–65% | Mineral such as aluminum oxide |
| 0.5–1.5% | Surfactant |
| .001–15% | Microcapsules with perfume. |

11. Perfume microcapsules obtained by evaporating a mixture made of:

| | |
| --- | --- |
| 35–40% | Decamethylcyclopentasiloxane |
| 25–30% | Oil base fragrance |
| 15–25% | Urea |
| 10–15% | Dietillphtalate |
| <2% | Water |
| <2% | Octamethylcyclotetrasiloxane |
| <1% | Methylsalicilate |
| <0.04% | Formaldehyde. |

12. The abrasive cleaning article made according to the process of claim 10.

* * * * *

UNITED STATES PATENT AND TRADEMARK OFFICE
CERTIFICATE OF CORRECTION

PATENT NO.       : 7,015,156 B2                                        Page 1 of 1
APPLICATION NO.  : 10/483880
DATED            : March 21, 2006
INVENTOR(S)      : Arellano, Raul Maldonado It is certified that error appears in the above-identified patent and that said Letters Patent is hereby corrected as shown below:

On the title Page item [75] (Inventors) -- Line 1 - After "Maldonado" delete "," and insert - - Arellano, - -, therefor.

Title Page item [75]: (Inventors) -- Line 2 - After "Perez" delete "," and insert - - Vazquez, - -, therefor.

title Page Col. 2 item [56]: (Foreign Patent Documents) -- Line 7 - Delete "54-4886" and insert - - 58-4886 - -, therefor.

Title Page Col. 2 item 57 (Abstract) -- Line 1 - After "The" delete "a".

Column 6 -- Line 36 - Delete "an d" and insert - - and - -, therefor.

Signed and Sealed this

Twenty-second Day of August, 2006

JON W. DUDAS
*Director of the United States Patent and Trademark Office*